(12) United States Patent
Doshi et al.

(10) Patent No.: US 6,365,131 B1
(45) Date of Patent: Apr. 2, 2002

(54) PHARMACEUTICAL DENTAL FORMULATION FOR TOPICAL APPLICATION OF METRONIDAZOLE BENZOATE, CHLORHEXIDINE GLUCONATE AND LOCAL ANESTHETIC

(75) Inventors: Madhukant Mansukhlal Doshi; Milind Dattatraya Joshi; Bharat Pravinchandra Mehta, all of Maharashtra (IN)

(73) Assignee: J. B. Chemicals & Pharmaceuticals Ltd., Mumbai (IN)

( * ) Notice: Subject to any disclaimer, the term of this patent is extended or adjusted under 35 U.S.C. 154(b) by 0 days.

This patent is subject to a terminal disclaimer.

(21) Appl. No.: 09/480,365

(22) Filed: Jan. 10, 2000

Related U.S. Application Data

(63) Continuation-in-part of application No. 08/962,099, filed on Oct. 31, 1997, now Pat. No. 6,017,516.

(51) Int. Cl.$^7$ .................. A61K 7/16; A61K 31/535; A61K 9/70; A61K 9/06; A61L 15/44

(52) U.S. Cl. .................. 424/49; 424/445; 424/447; 424/449; 514/239.2; 514/817; 514/944; 514/969

(58) Field of Search ................ 424/49–58, 445, 424/447, 449; 514/239.2, 817, 944, 969

(56) References Cited

U.S. PATENT DOCUMENTS

| | | | | |
|---|---|---|---|---|
| 5,013,545 A | * | 5/1991 | Blackman et al. | 424/81 |
| 5,230,895 A | * | 7/1993 | Czarnecki et al. | 424/422 |
| 6,017,516 A | * | 1/2000 | Mody et al. | 424/55 |

* cited by examiner

*Primary Examiner*—Shep K. Rose
(74) *Attorney, Agent, or Firm*—Lackenbach Siegel, LLP

(57) ABSTRACT

Pharmaceutical dental gel preparation comprising of metronidazole benzoate, chlorhexidine gluconate, and local anesthetic as the active ingredient; glycol as the solvent medium; a carboxyvinyl polymer, cross-linked polymer of acrylic acid copolymerized with polyalkylsucrose as a gelling agent.

21 Claims, No Drawings

PHARMACEUTICAL DENTAL FORMULATION FOR TOPICAL APPLICATION OF METRONIDAZOLE BENZOATE, CHLORHEXIDINE GLUCONATE AND LOCAL ANESTHETIC

Cross Reference to Related Application

This Application is a Continuation-In-Part of U.S. patent application Ser. No. 08/962,099 filed Oct. 31, 1997 now U.S. Pat. No. 6,017,516.

FIELD OF THE INVENTION

The present invention relates to preparation of pharmaceutical dental gel formulation for topical application of metronidazole benzoate and chlorhexidine gluconate and local anesthetic for the treatment of gingivitis and periodontitis.

DESCRIPTION OF THE PRIOR ART

The organism most often encountered in oral infections is viridans streptococci, a verity of anaerobes, and facultative streptococci. Anaerobes isolated from dentoalveolar abscesses were generally susceptible to benzylpenicillin, amoxycillin, erythromycin, clindamycin and metronidazole. Dental caries is caused by the erosion of tooth enamel due to acid produced by bacteria (especially streptococcus mutans) in plaque. Fluoride in various forms is used in dental caries prophylaxis, where it may promote remineralisation or reduce acid production by plaque bacteria. Periodontal diseases encompasses specific conditions affecting the gingiva and the supporting connective tissue and alveolar bone. Gingivitis is thought to be caused by a non-specific bacterial plaque flora that gradually changes from predominantly Gram-positive to more Gram-negative. Gingivitis may or may not develop into periodontitis, but periodontitis is always preceded by gingivitis. Priodontitis is associated with Gram-negative microflora.

Most gingivitis and periodontitis can be prevented and treated by adequate oral hygiene and plaque removal using mechanical means such as toothbrushes. Mechanical removal of calculus is necessary where the build up is significant. Disinfectants and other agents such as cetylpyridinium chloride or chlorhexidine also help to reduce plaque accumulation.

Metronidazole is a 5-nitroimidazole derivative with activity against anaerobic bacteria and protozoa. Its mechanism of action is thought to involve interference with DNA by a metabolite in which the nitro group of metronidazole has been reduced by bacterial nitroreductases to an unstable intermediate, which interacts with DNA, effectively preventing further replication.

Metronidazole is bactericidal. Minimum inhibitory concentration (MIC) for susceptible anaerobic bacteria generally ranges from 0.1 to 8 ugm/ml. It also has activity against the facultative anaerobes *Gardnerella vaginalis* and *Helicobacter pylori* and against some spirochetes. Moreover it is active against several protozoa and anaerobic bacteria, including Bacteroides and Clostridium sp. is sensitive in vitro to metronidazole. Metronidazole is also used in the treatment and prophylaxis of anaerobic bacterial infections. Activity of metonidazole against obligate anaerobic bacteria in vitro including the Gram-negative organisms *Bacteroides fragilis* and other Bacteroides sp., Fusobacterium sp., and Villanelle sp. and the Gram-positive organisms *Clostridium difficile, Cl. pergringens*.

Metronidazole is administered by mouth in tablets or as metronidazole benzoate, in oral suspension. The tablets are taken with or after food and the suspension is taken at least 1 hr before food. Metronidazole is also given rectally in suppositories, applied topically as a gel, or administered by intravenous infusion of metronidazole or metronidazole hydrochloride.

This gel when applied on the affected part, flows and fills out the gingival pocket after application, thereby comes in contact with the aqueous part of either gingival cravicular fluid or saliva containing esterases which hydrolyse metronidazole benzoate to free active metronidazole which exerts it activity on anaerobic bacteria present it periodontal region.

The long term use of oral metronidazole in chronic condition like periodontal diseases may be associated with certain side effects such as gastro-intestinal disturbances, nausea, an unpleasant metallic taste, anorexia, vomiting, diarrhea, dry mouth, a furried tounge and glossitis. However, to avoid the drawbacks of systemic administration, a dental gel for topical application of metronidazole is desirable in periodontitis.

A dental gel comprising of metronidazole benzoate 25% used for gingivitis and periodontitis, and its topical use seems to be as effective as conventional therapy in the treatment of adult periodontitis. (J. Clin. Periodontal 1992, :19, 715–729). The use of metronidazole benzoate 25% dental gel is associated with a limitation viz. when applied subgingivally, the active drug reaches sulcus for which special injector is required and the procedure is cumbersome and is done by dental surgeon only.

A dental gel comprising of chlorhexidine is also used for gingivitis and prevention of plaque. Chlorhexidine is a bisbiguanide antiseptic and disinfectant effective against a wide range of bacteria, some fungi, and some viruses. It is used in various preparations as the acetate or gluconate commonly with cetrimide, for disinfection of skin, wounds, burns. The dental gel or mouthwash comprising of chlorhexidine may discolour the tounge or teeth. Chlorhexidine is bactericidal or bacteriostatic against a wide range of Gram-positive and Gram-negative bacteria. It is more effective against Gram-positive than Gram-negative bacteria. Chlorhexidine is most active at a neutral or slightly acid pH.

Similarly a dental composition consisting of chlorhexidine gluconate in various strengths of 0.1 to 1% in the form of topical application also used for periodontal diseases (Br. Dental J. 1977, 142, 366–369). Chlorhexidine gluconate is also used in a 1% dental gel and 0.2% mouthwash for the prevention of plaque and the prevention and treatment of gingivitis and in the treatment of oral candidiasis.

Lidocaine is a local anaesthetic of the amide type and is widely used in injection and for local application to mucous membranes. It has rapid onset of action and anesthesia is obtained within a few minutes depending on the site of administration. It has an intermediate duration of action.

Benzocaine is ethyl ester of p-Aminobenzoic acid. It is usually used to relieve pain associated with ulcers, wounds and mucous membrane. Normally it acts only as long as it is in contact with skin or mucosal surface. Peak effect occurs within 1 min after the application and lasts for 36 to 60 min.

Thus taking into consideration the limitation and disadvantages associated with the conventional dental gels, the inventor has come out with a unique dental gel composition comprising of metronidazole benzoate and chlorhexidine gluconate & local anaesthetic in the form of aqueous gel having the effect on aerobic and anaerobic bacteria in periodontal diseases and this combination has been found to be therapeutically better over either metronidazole benzoate or chlorhexidine gluconate individually.

This application is continuation-in-part of the U.S. patent application Ser. No. 08/962,099 filed dated Oct. 31, 1997 claming dental gel comprising of metronidazole benzoate, chlorhexidine gluconate used for gingivitis and periodontitis.

The present application relates to the preparation of dental gel having the same composition as in U.S. patent application Ser. No. 08/962,099 with additional ingredient viz. local anaesthetic. The advantage of local anesthetics is, it reversibly blocks impulse conduction in any part of the nervous system and in all nerves, including sensory, motor and autonomic types, producing a transient loss of sensation in a circumscribed area of the body without causing a general loss of consciousness. This action is used to block the pain sensation to the areas where it is applied, hence it is useful to prevent pain in dental manipulations, injury and diseases.

Accordingly, it is among the objects of the present invention to provide dental gel formulations containing metronidazole benzoate, chlorhexidine gluconate and local anesthetic, which are stable, which may be readily employed without pain and other side effects or other undesirable characteristics.

DETAILED DESCRIPTION OF THE INVENTION

The present invention relates to the pharmaceutical dental gel formulation for topical application in the form of aqueous gel suitable for the treatment of periodontal diseases. The present formulation comprises of Metronidazole benzoate, chlorhexidine gluconate (20% solution), the active ingredient is incorporated in the dental gel formulations of the present invention in an amount of about 0.5 to 3.0% and 0.2 to 2 percent by the weight respectively, preferably from about 1% of active metronidazole and 0.25% active chlorhexidine by weight respectively.

The concentration of local anesthetic, especially lidocaine may fluctuate between 0.5 to 2 weight % in terms of lidocaine hydrochloride. The addition of a local anesthetic is not undesired also for medical reasons, for the prevention of dental pain. Preferred concentration is 0.5%.

Just like the lidocaine most of the local anesthetics are slightly basic substances forming salts with acids such as hydrochloride. The local anesthetics are expediently used in the form of their hydrochloride salt. Local anesthetics of the kind of lidocaine are, in particular, etidocaine, benzocaine. The concentration of benzocaine as a local anesthetic may fluctuate in the range of 1 to 20%, however preferred concentration is 7.5%.

As indicated hereinabove, the medium for the active ingredient comprises a mixture of water and propylene glycol. Propylene glycol concentration fluctuates between 5 to 80%. Preferred concentration is 5% by weight based on the total weight of the said composition. Other medium can be used in this specification refers to Glycerin, Polyethylene glycols, but preferred is propylene glycol.

The carboxyvinyl polymer used, as the gelling agent in the present invention is a hydrophilic polymer obtained by the polymerization of acrylic acid as the principal component. Preferred molecular weight of the polymer is in the range of $4 \times 10^6$. Polymer present in the composition is in the range of 0.2 to 7% by weight based on the total weight of the said composition. Preferred polymer is carbomer 940 in concentration of which better results were obtained is 1.5%.

Other polymer used for said gelling agent in the present invention is selected from carbomer 940, carbomer 934, Hydroxypropylmentylcellulose, sodium carboxymethylcellulose.

If the pH of the gel formulation of the present invention is in considerably acidic or basic side then it is desirable to add the pH modifier to the preparation of the present invention to adjust its pH in the range of 4.5–7, preferably 5 to 6. There are no specific limitations as to the kind of the pH modifiers are inorganic pH modifier, e.g. sodium hydroxide or potassium hydroxide. Preferred pH modifier in the present invention is sodium hydroxide solution.

An auxilliary agents used in the present invention is comprised of disodium EDTA, menthol, and sodium saccharine, were added to the gel preparation of this invention. Menthol imparts the cooling effect, EDTA acts as chelating agent and antioxidant, and sodium saccharine gives the sweetness to the dental gel. It is suitably incorporated in an amount of from about 0.025 to 0.5 percent by weight of the preparations.

Chelating agent used in this specification refers to disodium EDTA, Edetic acid, citric acid, Disodium calcium EDTA. Flavouring agent which imparts soothing action refers to menthol, peppermint oil, spearmint oil, Anis oil, clove oil. Sweetening agent here refers to Saccharine sodium, Aspartarnt Dihydrochalcones, D-tryptophan etc.

The present invention will now be further illustrated by, but is by no means limited to, the following examples wherein preferred embodiments of the metronidazole benzoate and chlorhexidine gluconate and local anesthetic containing dental gel preparations are expressed on the weight basis. Those who are skilled at the art can decide the percentage of other/auxilliary agents used to formulate the different example described below.

EXAMPLE 1

| Active ingredient | |
| --- | --- |
| Metronidazole | 1.0% |
| (as Metronidazole benzoate) | |
| Chlorhexidine gluconate | 0.25% |
| (20% solution) | |
| Lidocaine hydrochloride | 0.5% |
| Other agents | |
| Propylene glycol | 5.0% |
| Carbomer 940 | 1.5% |
| Disodium EDTA | 0.025% |
| Sodium saccharine | 0.1% |
| Menthol | 0.5% |
| Purified water | q.s. |
| Sodium hydroxide | pH modifier |

Preparation Method:

The gel preparations of the invention can be prepared for example, by initially dissolving menthol in propylene glycol to this solution active metronidazole is added in portion with continuous stirring. Add carboxyvinyl polymer (carbomer 940) in portion with continuous stirring with homoginizer to form gel at 30 to 35° C. To the gel thus obtained is added a separately prepared aqueous solution of disodium EDTA, sodium saccharin, lidocaine hydrochloride and chlorhexidine gluconate with stirring till it dissolve. Further, sodium hydroxide, pH modifier is added to the resulting gel preparation, with stirring, in an amount sufficient to adjust the pH of the resulting gel preparation to about 5 to 6 which will form uniform viscous gel.

EXAMPLE 2

| | |
|---|---|
| Metronidazole (as Metronidazole benzoate) | 0.5% |
| Chlorhexidine gluconate (20% solution) | 0.2% |
| Benzocaine | 10% |

The same procedure used in Example 1 was repeated, only change is benzocaine was dissolved in glycol medium.

EXAMPLE 3

| | |
|---|---|
| Metronidazole (as Metronidazole benzoate) | 1.0% |
| Chlorhexidine gluconate (20% solution) | 0.25% |
| Benzocaine | 7.5% |

The same procedure used in Example I were repeated, only change is benzocaine was dissolved in glycol medium.

EXAMPLE 4

| | |
|---|---|
| Metronidazole (as Metronidazole benzoate) | 0.5% |
| Chlorhexidine gluconate (20% solution) | 2.0% |
| Lidocaine hydrochloride | 1.0% |

The same procedure used in Example 1 was repeated.

EXAMPLE 5

| | |
|---|---|
| Metronidazole (as Metronidazole benzoate) | 3.0% |
| Chlorhexidine gluconate (20% solution) | 2.0% |
| Benzocaine | 10.0% |

The same procedure used in Example 1 was repeated, only change is benzocaine was dissolved in glycol medium.

EXAMPLE 6

| | |
|---|---|
| Metronidazole benzoate (as Metronidazole benzoate) | 2.0% |
| Chlorhexidine gluconate (20% solution) | 2.0% |
| Lidocaine hydrochloride | 1.0% |

The same procedure used in Example 1 was repeated.

All the gel preparations hereof has good stability. They do not show any substantial changes in viscosity at little higher temperature or other physical changes.

It is to be understood that the example and embodiments described hereinabove are for the purpose of providing a description of present invention by way of example and are not to be viewed as limiting the present invention in any way. Those who are skilled in the art can make various modifications or changes that may be made to the described invention and are also contemplated by it which can be included within the spirit and purview of this application.

Clinical Trials

To investigate the effectiveness of the present invention in periodontitis and other related diseases like dry sockets and apthous ulcer stomatitis, multicentric controlled clinical trials were carried out at five different centers all over India. Number of patients of different age groups were included in the trial.

These study is not disclosed to the public and the trials were done in confidence. The results of clinical study in India is given below:

1. In this study 50 patients having chronic gingivitis were considered and divided into 2 groups of 25 each. One group receives scaling as a treatment and other group received scaling plus formulation of present invention, twice a day for 2 weeks. On follow-up it was found that patients maintained on scaling plus the formulation of present invention were recovered faster in respect to bleeding on probing and probing pocket depth. The size of the pocket reduced faster with the present formulation as compared to group subjected to scaling. However, there is no feeling of dental pain. This indicates that application of present formulation was found to be superior to scaling alone in chronic gingivitis.

2. 40 patients suffering from acute ulcer gingivitis were included in the trial and they were divided into 2 groups. Group one received chlorhexidine 0.25% gel twice daily and other group received the gel of the present invention twice daily. In both the group through debridment was carried out. The group of the present formulation showed improvement much faster as compared to the group of 0.25% chlorhexidine gel alone. However in both the group gingivectomy was not required, and no complaint of pain was observed. This clearly indicates that present formulation is better choice than chlorhexidine alone.

3. 30 patients suffering from chronic periodontitis were included in the trial and divided into 2 groups of 15 each. One group received scaling and chlorhexidine gel 0.25% as a treatment whereas other group receiving scaling plus the present formulation. The group received gel of the present formulation showed faster improvement in probing pocket depth and bleeding on probing compared to scaling and chlorhexidine and no evidences of the dental pain.

4. Study was carried out on 30 patients undergoing extractions of tooth. They divided into 2 groups of 15 each. One group received the present formulation of dental gel twice daily whereas other group received only analgesic. The group receiving the present composition did not develop any dry socket whereas the group treated with only with analgesic shows dry socket in 4 patients. This clearly indicates the usefulness of the present dental gel formulation and is better than analgesic alone.

5. In this study 20 patients were included suffering from recurrent apthous stomatitis (Ulcer) and divided into 2 groups of 10 each. Group 1 was treated with dental gel formulation of present invention twice daily and other group was treated with analgesic and 0.25% chlorhexidine gluconate gel. The group treated with present formulation showed faster healing of ulcer and relief from pain compared to patients with analgesic and 0.25% chlorhexidine gluconate gel.

6. In this study 30 patients were included suffering from periodontitis were included in the trial and divided into 2 groups of 15 each. One group received scaling and formulation of Lidocaine hydrochloride (2%) and Chlorhexidine gluconate (0.25%) whereas other group receiving scaling plus the present formulation. The group receiving the gel of present invention twice daily showed faster improvement in probing pocket depth and in both the cases there is no evidence of dental pain.

7. Study carried out on 20 patients undergoing extractions of tooth. They divided into 2 groups of 10 each. One group received the formulation of local anesthetic whereas other group received the formulation of the present invention. The group receiving the present formulation did not develop any dry socket as against other group which shows dry socket in 6 patients. This indicates the advantage of the present dental gel.

Above clinical trials confirms the efficacy of the present dental gel formulation of this invention in following conditions like.

a. Chronic gingivitis (Edematous, Hyperplastic and Atrophic)
b. Acute ulcerative gingivitis
c. Chronic periodontitis
d. To prevent post extraction infections (dry socket)
e. In recurrent apthous stomatitis (Ulcer)
f. Dental pain due to infections.

What is claimed is:

1. A pharmaceutical dental gel formulation for topical application in the form of an aqueous gel comprising a therapeutically effective amount of metronidazole benzoate, chlorhexidine gluconate, and a local anesthetic gelled with a hydrophilic polymer, an aqueous medium, a chelating agent, a sweetening agent, a flavoring agent, and a pH modifier.

2. A pharmaceutical dental formulation in accordance with claim 1, wherein metronidazole benzoate is present in an amount from about 0.5% to about 3.0% based on the total weight of the composition, and chlorhexidine gluconate is present in an amount from about 0.2% to about 2% based on the total weight of the composition.

3. A pharmaceutical dental formulation in accordance with claim 2, wherein metronidazole benzoate is about 1% of the total weight of the composition, and chlorhexidine gluconate is about 0.25% of the total weight of the composition.

4. A pharmaceutical dental formulation in accordance with claim 2, wherein metronidazole benzoate is present in an amount from at least about 1% of the total weight of the composition, and chlorhexidine gluconate is present in an amount from at least about 0.25% of the total weight of the composition.

5. A pharmaceutical dental formulation in accordance with claim 1, wherein said local anesthetic is lidocaine.

6. A pharmaceutical dental formulation in accordance with claim 5, wherein said lidocaine is lidocaine hydrochloride present in an amount from about 0.5% to about 2% by weight of dry powder based on the total weight of the composition.

7. A pharmaceutical dental formulation in accordance with claim 5, wherein said lidocaine is lidocaine hydrochloride present in an amount of about 0.5% by weight of powder based on the total weight of the composition.

8. A pharmaceutical dental formulation in accordance with claim 1, wherein the hydrophilic polymer is selected from the group consisting of carbomer 940, carbomer 934, Hydroxypropylmethylcellulose, sodium carboxymethylcellulose, and combinations thereof, and wherein the hydrophilic polymer is present in an amount from about 0.2% to about 7% by weight based on the total weight of said composition.

9. A pharmaceutical dental formulation in accordance with claim 8, wherein said hydrophilic polymer is carbomer 940 in an amount of about 1.5% by weight based on the total weight of the said composition.

10. A pharmaceutical dental formulation in accordance with claim 1, wherein said aqueous medium comprises water and glycol.

11. A pharmaceutical dental formulation in accordance with claim 10, wherein said glycol is selected from the group consisting of propylene glycol, glycerin, polyethylene glycols, and combinations thereof.

12. A pharmaceutical dental formulation in accordance with claim 11, wherein said glycol is propylene glycol present in a range of about 5% to about 80% by weight based on the total weight of said composition.

13. A pharmaceutical dental formulation in accordance with claim 1, wherein said chelating agent is selected from the group consisting of Disodium EDTA, Edetic acid, Citric acid, Disodium calcium EDTA, and combinations thereof.

14. A pharmaceutical dental formulation in accordance with claim 13, wherein said chelating agent is Disodium EDTA, in the range of about 0.01% to about 0.1% by weight based on the total weight of said composition.

15. A pharmaceutical dental formulation in accordance with claim 1, wherein said sweetening agent is selected from the group consisting of saccharine sodium, Aspartame, Dihydrochalcones, d-tryptophan, and combinations thereof.

16. A pharmaceutical dental formulation in accordance with claim 15, wherein said sweetening agent is saccharine sodium.

17. A pharmaceutical dental formulation in accordance with claim 1, wherein said flavoring agent is selected from the group consisting of menthol, peppermint oil, spearmint oil, Anis oil, clove oil, and combinations thereof.

18. A pharmaceutical dental formulation in accordance with claim 17, wherein said flavoring agent is menthol.

19. A pharmaceutical dental formulation in accordance with claim 1, having pH in the range of about 4.5 to about 7.

20. A pharmaceutical dental formulation in accordance with claim 13, wherein such chelating agent is Disodium EDTA present in an amount of about 0.025% by weight based on total weight of said composition.

21. A pharmaceutical dental formulation in accordance with claim 1, wherein the said local anesthetic is benzocaine.

* * * * *